United States Patent [19]

Oertli

[11] Patent Number: 5,346,491

[45] Date of Patent: Sep. 13, 1994

[54] FEED DEVICE FOR BIPOLAR ELECTRODES FOR CAPSULOTOMY

[75] Inventor: Heinz A. Oertli, Teufen, Switzerland

[73] Assignee: Sony Corporation, Tokyo, Japan

[21] Appl. No.: 788,808

[22] Filed: Nov. 7, 1991

[30] Foreign Application Priority Data

Mar. 28, 1991 [CH] Switzerland .................. 965/91

[51] Int. Cl.$^5$ ............................................. A61B 17/39
[52] U.S. Cl. ........................................ 606/37; 606/39; 606/40
[58] Field of Search ................ 606/37, 41, 42, 48, 606/50, 51, 39, 40, 20, 29, 32, 45, 219, 236; 128/804

[56] References Cited

U.S. PATENT DOCUMENTS

| | | | |
|---|---|---|---|
| 4,211,230 | 7/1980 | Woltosz | 606/40 |
| 4,378,801 | 5/1983 | Oosten | 606/37 |

Primary Examiner—Lee S. Cohen
Assistant Examiner—Marianne Parker
Attorney, Agent, or Firm—Lewis H. Eslinger; Jay H. Maioli

[57] ABSTRACT

A pulsed high frequency current is fed to a bipolar diathermy instrument for optimum execution of a section in capsulotomy. The pulse duration can constantly be altered between 3 ms and 11 ms, whereby a pause of 30 ms or 22 ms develops. This pause is sufficient to cool the instrument tip, flushed with sodium chloride, in order to prevent the possibility of injury to adjacent tissue. The pulse repetition frequency is about 15 hz. The device necessary for the purpose includes pulse duration control (31) and HF oscillator (30). The HF current is synchronized by pulses from control (31) with AND gate (35). Amplifier (40) feeds handpiece (21) of the diathermy instrument by transformer (46). The required operation free from grounding is thereby assured.

16 Claims, 2 Drawing Sheets

FEED DEVICE FOR BIPOLAR ELECTRODES FOR CAPSULOTOMY

BACKGROUND OF THE INVENTION

The present invention relates to a feed device.

Bipolar wet field diathermy in microsurgery is described in "Klinische Monatsblätter für Augenheilkunde" (Clinical Ophthalmology Monthly), May, 1984, vol. 5, pp. 331-512. The possibility of hemostasis in the vitreous humor was investigated, starting with the first vitrectomies in 1972. A coaxial bipolar diathermy device was developed as a suitable instrument for the purpose. However, it is necessary to make sure that the heating is not too high for operations on the eye. The device was consequently equipped with an aspiration infusion irrigation device at that time to remove emerging liquid blood. It was possible to close the then visible hemorrhage source by coagulation.

It was then almost logical to replace the previous procedure for opening the capsule of the lens, namely that of cutting open the capsule sac, opening the capsule sac by perforation and then tearing, or by capsulorhexis, by a diathermy technique.

Two instruments were disclosed for the diathermic opening of the capsule sac.

In U.S. Pat. No. 4,367,744, an electrically insulating handpiece carries a cauterizing ring, which is fed with electric power to the handpiece from behind by one wire. In order for it to be possible for a current to flow, it was proposed to conduct the procedure with two wires to the cauterizing loop. On applying the cauterizing loop to the lenticular sac, the current produces heat in a range of from 500° C. to 2000° C. Such a high temperature may act for only a short time, and the cauterized site on the lenticular sac must be cooled as quickly as possible. Because the cauterizing loop must be introduced into the eye in already hot state in order to be able to perform the operation in as short a time as possible, it is necessary to proceed extremely carefully, in order not to injure any other parts of the eye.

U.S. Pat. No. 4,481,948 describes a cauterizing loop of similar type, but which is not heated with current flowing in the loop. A high-frequency 10 khz current is instead fed to the loop. An opposite pole is placed beneath the patient in order to close the circuit. The physician switches on the high-frequency circuit by means of a pedal.

High heat, which can be very injurious to the eye tissue, can also result with this arrangement. According to the older patent, the hot loop had to be introduced into the aqueous chamber until it could then be placed through the pupil into the posterior chamber onto the lenticular sac, in order to cauterize an opening there.

It is possible to activate, i.e., heat the loop with the high-frequency current as desired by the physician. The high-frequency current then can flow only when the loop is placed on a site covered with conducting liquid, thus on the lenticular sac. It is not possible to control the heat acting to produce coagulation at the border of the opening by this effect, so that mild injuries can result from the action of the heat.

Consequently, an object of the invention is that of controlling the current feed so that only precisely as much heat is produced for cutting the lenticular sac and coagulating the border of the hole, but protecting other tissues against heat action without additional feed.

BRIEF DESCRIPTION OF DRAWINGS

The invention is illustrated with the aid of drawings in an execution example below. The following features are shown.

DESCRIPTION OF PREFERRED EMBODIMENT

Figure 1:
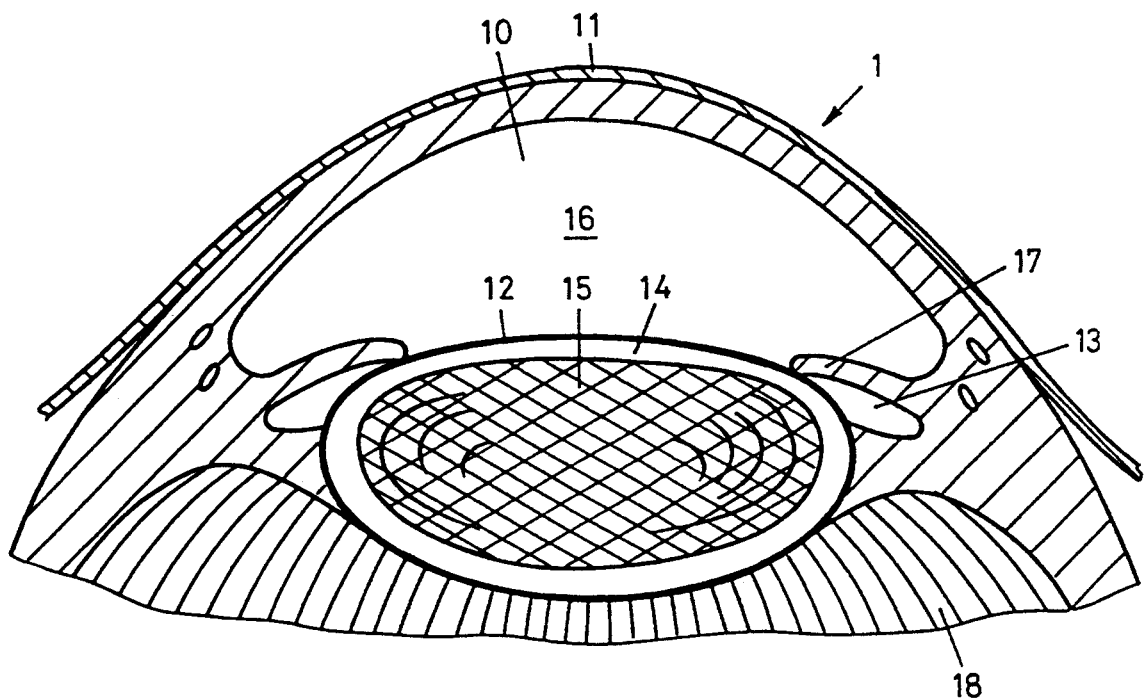
FIG. 1 an enlarged segment of a human eye in section view.

FIG. 1 shows a front section of human eye 1 in greatly enlarged scale. This section clearly shows aqueous chamber 10, which is sealed off outside by cornea 11. The lenticular capsule consists of capsule sac 12, nucleus lentis 15, and cortex 14 lying between. Dilated iris 17 lies above. Pupil 16 forms a large opening. Posterior chamber 13 is located behind iris 17. Lenticular sac 12 with lens 15 lies between iris 17 and sclera 18.

Figure 2:
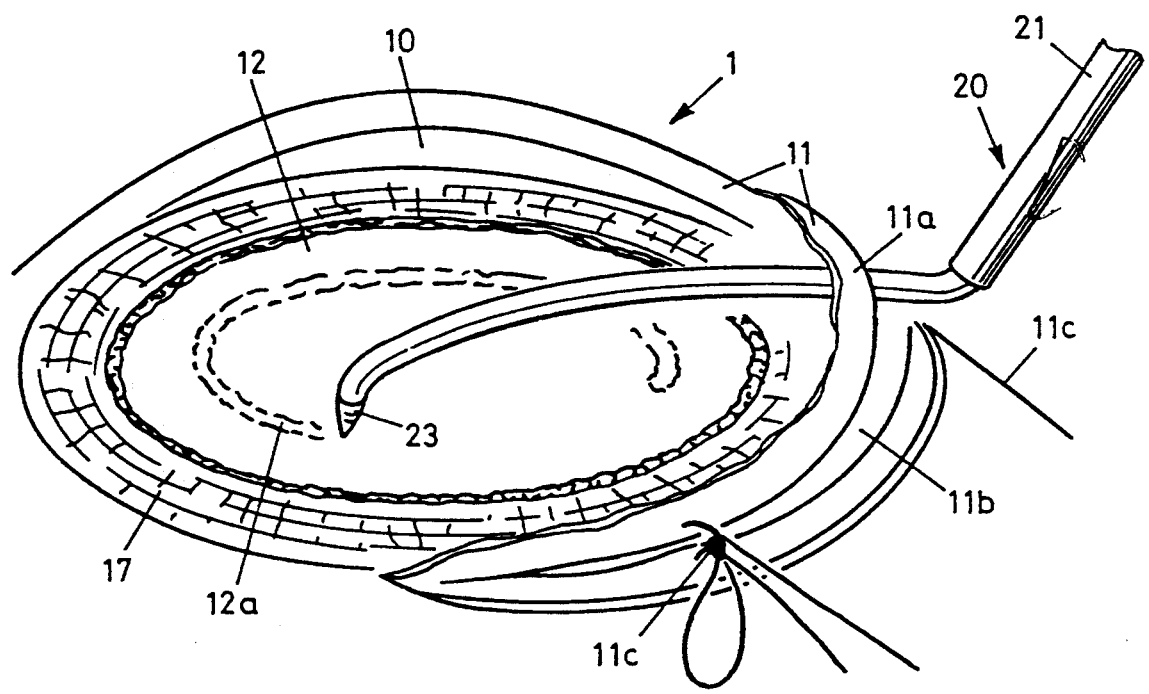
FIG. 2 the same segment in perspective view with a bipolar diathermy instrument for capsulotomy.

FIG. 2 shows a view of eye 1 after FIG. 1 from obliquely above, so that the entire iris 17 is visible. Cornea 11 is sectioned at its edge 11a in order to create an access to aqueous chamber 10. Section 11b is held together by loop 11c on both sides, so that it cannot tear. Bipolar diathermy instrument 20 is introduced through this slit with handpiece 21, from which bipolar tip 23 protrudes. This bipolar tip 23 is bent in order for the instrument to be introduced at the side of eye 1 and parallel to lenticular sac 12 up to the section site, where section 12a can then be made in lenticular sac 12 with bent tip 23.

The physician can now coagulate lenticular sac 12 with high-frequency current reaching bipolar tip 23, or coagulate and sever with higher electrical feed. The severing runs into the difficulty mentioned at the outset, due to strong heating of the area around the working field.

Figure 3:
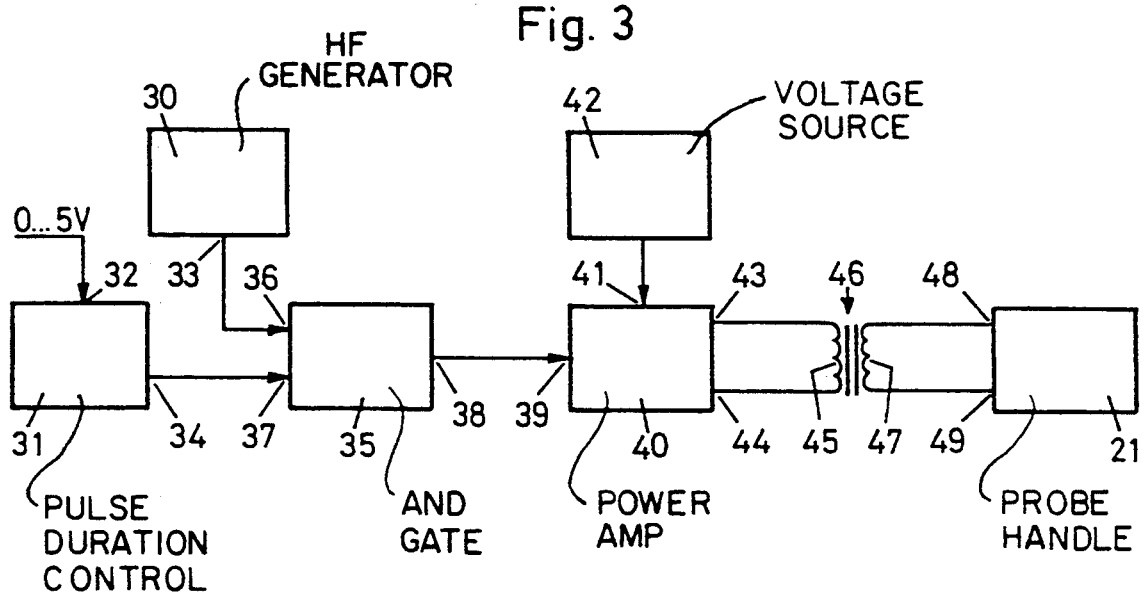
FIG. 3 block diagram of a feed device for the bipolar diathermy instrument.

A feed device (FIG. 3) with which a pulse duration modulation high-frequency current can be produced is now provided according to the invention. The feed device accordingly includes high-frequency generator 30 and pulse duration control 31, which is fed at rated value input 32 with a control voltage of 0 to +5 v, for example. The output 33 of high-frequency generator 30 and the output 34 of pulse duration control 31 are fed to inputs 36 and 37 of AND gate 35, whose output 38 is connected to input 39 of power amplifier 40. Power amplifier 40 is fed at input 41 from stabilized voltage source 42. The voltage source provides a current of 3 amp. at 18-v voltage. It includes short-circuit monitoring. Outputs 43, 44 are fed to the primary winding 45 of transformer 46. Lines 48, 49 lead from its secondary winding 47 to handpiece 21 of bipolar diathermy instrument 20.

Figure 4:
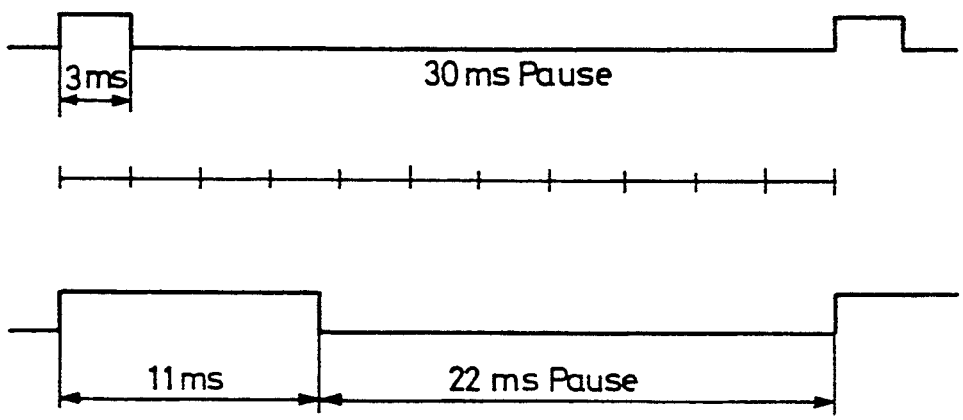
FIG. 4 two pulse diagrams for current flow from the feed device.

It is possible to synchronize the high-frequency voltage with a frequency of 500 khz, for example, by this arrangement by selecting a control voltage of from 0 to 5 v, so that a constant frequency rectangular signal with a frequency of 30 hz and consequently with a pulse duration $t_p$ of 3 to 11 ms and a pulse pause $t_i$ of 22 to 30 ms is produced at a control voltage of 0.5 to 5 v, with which the AND gate is synchronized. At higher control voltage, the pulse becomes longer and the pulse pause correspondingly shorter (FIG. 4). The frequency of the rectangular oscillation remains constant. Power amplifier 40 can be fed by connection in AND gate 35. It can release a pulse output of $P_{max}=54$ w by means of the stabilized voltage. The tissue of the lenticular sac is severed by this high pulse output, so that more than coagulation is achieved. The method of feeding high-frequency pulses with a pulse pause which lasts at least twice as long as the pulse permits a sufficiently long cooling not to endanger the adjacent tissue. The capsulotomy handpiece is insulated from the device by the transformer, so that no potential burdened with grounding is present in this instrument. An ionizing solution, for example Healon, is required in order for the high-frequency current to be able to flow at all between the poles of the bipolar diathermy instrument.

I claim:

1. An electrical capsulotomy device for eye microsurgery, comprising:
    a bipolar diathermy instrument;
    a high-frequency generator producing an output signal;
    modulating means for modulating said output signal from said high-frequency generator and producing a modulated output signal at an output thereof;
    said modulating means operating to periodically interrupt passage of said high-frequency output signal according to a predetermined duty cycle;
    said duty cycle having a pulse duration time $t_p$ and a pulse pause time $t_i$ according to the relationship $$2 \leq t_i/t_p \leq 10;$$

a power amplifier having an input connected to said output of said modulating means and receiving said modulated output signal from said modulating means for producing an output therefrom; and
    a transformer having a primary winding connected to the output of said power amplifier and having a secondary winding connected to said bipolar diathermy instrument.

2. An electrical capsulotomy device in accordance with claim 1, further comprising a pulse duration control device having an output, and wherein said modulating means comprises an AND gate having a first input connected to receive said output signal of said high-frequency generator and a second input connected to said output of said pulse duration control device.

3. An electrical capsulotomy device in accordance with claim 1, wherein said pulse duration time $t_p$ is substantially equal to 3 ms.

4. An electrical capsulotomy device in accordance with claim 1, characterized by the fact that said pulse pause time $t_i$ is substantially equal to 30 ms.

5. An electrical capsulotomy device in accordance with claim 1, further comprising a stabilized voltage source and wherein said power amplifier is fed from said stabilized voltage source.

6. An electrical capsulotomy device in accordance with claim 1, wherein said high-frequency generator generates a signal with a frequency substantially equal to 500 kHz.

7. An electrical capsulotomy device in accordance with claim 1, wherein said power amplifier releases a pulse output of Pmax=54 W.

8. An electrical capsulotomy device for eye microsurgery comprising:
    a bipolar diathermy instrument;
    an AND gate;
    a pulse duration control device that generates a square wave voltage having a predetermined duty cycle having an output;
    a high-frequency generator having an output signal connected to a first input of said AND gate whose second input is connected to said output of said pulse duration control device;
    said AND gate operating to periodically allow and interrupt the passage of said output signal from said high-frequency generator according to said predetermined duty cycle;
    said duty cycle having a pulse duration time $t_p$ and a pulse pause time $t_i$ according to the relationship $$2 \leq t_i/t_p \leq 10;$$

a power amplifier having an input connected to an output of said AND gate; and
    a transformer having a primary winding connected to an output of said power amplifier and a secondary winding connected to an input of said bipolar diathermy instrument.

9. An electrical capsulotomy device in accordance with claim 8, wherein said pulse duration time $t_p$ is substantially equal to 3 ms.

10. An electrical capsulotomy device in accordance with claim 8, wherein said interruption time $t_i$ is substantially equal to 30 ms.

11. An electrical capsulotomy device in accordance with claim 8, further comprising a stabilized voltage source and wherein said power amplifier is fed from said stabilized voltage source.

12. An electrical capsulotomy device in accordance with claim 8, wherein said high-frequency generator generates a signal with a frequency substantially equal to 500 kHz.

13. An electrical capsulotomy device in accordance with claim 8, wherein said power amplifier releases a pulse output of Pmax=54 W.

14. An electrical capsulotomy device for eye microsurgery, comprising:
    a bipolar diathermy instrument;
    an AND gate;
    a pulse duration control device that generates a square wave voltage having a predetermined duty cycle having an output;
    a high-frequency generator having an output connected to a first input of said AND gate whose second input is connected to said output of said pulse duration control device;
    said AND gate operating to periodically allow and interrupt passage of said output from said high-frequency generator according to said predetermined duty cycle;
    said duty cycle having a pulse duration time $t_p$ and a pause time $t_i$, wherein the pulse duration time $t_p$ is of the order of magnitude of 3 milliseconds;
    a power amplifier having an input connected to an output of said AND gate; and
    a transformer having a primary winding connected to an output of said power amplifier and having a secondary winding connected to an input of said bipolar diathermy instrument.

15. An electrical capsulotomy device in accordance with claim 14, wherein said pulse pause time $t_i$ is substantially equal to 30 milliseconds.

16. An electrical capsulotomy device in accordance with claim 14, further comprising a stabilized voltage source and wherein said power amplifier is fed from said stabilized voltage source and said high-frequency generator generates a signal with a frequency of the order of magnitude of 500 kHz.

* * * * *

UNITED STATES PATENT AND TRADEMARK OFFICE
CERTIFICATE OF CORRECTION

PATENT NO. : 5,346,491
DATED : September 13, 1994
INVENTOR(S) : Heinz A. Oertli

It is certified that error appears in the above-identified patent and that said Letters Patent is hereby corrected as shown below:

On the title page after "[73] Assignee:"
change "Sony Corporation, Tokyo, Japan" to
-- Oertli-Instrumente AG, Berneck, Switzerland--.

Signed and Sealed this

Twenty-seventh Day of May, 1997

Attest:

BRUCE LEHMAN

*Attesting Officer*   *Commissioner of Patents and Trademarks*